United States Patent [19]

Anderson et al.

[11] Patent Number: 5,686,387
[45] Date of Patent: Nov. 11, 1997

[54] COMPOSITIONS CONTAINING SEMICARBAZONES

[75] Inventors: Richard J. Anderson, Palo Alto; Ian S. Cloudsdale, Boulder Creek; Robert J. Lamoreaux, San Juan Batista, all of Calif.; Kristine Schaefer, Adel, Iowa; Jost Harr, Oberwil, Switzerland

[73] Assignee: BASF Aktiengesellschaft, Ludwigschafen, Germany

[21] Appl. No.: 479,273

[22] Filed: Jun. 7, 1995

Related U.S. Application Data

[63] Continuation of Ser. No. 400,420, Mar. 3, 1995, Pat. No. 5,665,673, which is a continuation of Ser. No. 156,503, Nov. 23, 1993, abandoned, which is a continuation-in-part of Ser. No. 972,056, Nov. 5, 1992, abandoned, which is a continuation of Ser. No. 704,684, May 17, 1991, abandoned, which is a continuation of Ser. No. 490,792, Mar. 8, 1990, abandoned, which is a continuation-in-part of Ser. No. 291,850, Dec. 29, 1988, abandoned.

[51] Int. Cl.$^6$ .................. A01N 43/40; A01N 43/72; A01N 37/10; A01N 39/02

[52] U.S. Cl. .................. 504/130; 504/138; 504/144; 504/145; 504/146; 71/DIG. 1

[58] Field of Search ........................ 504/130, 145, 504/146, 138, 144; 71/DIG. 1

[56] References Cited

FOREIGN PATENT DOCUMENTS 0219451  4/1987  European Pat. Off. .

OTHER PUBLICATIONS

The Agrochemicals Handbook, Unwin Bros. Ltd., Surrey (England), 1983, p. A111/Oct. 83.

*Primary Examiner*—John Pak
*Attorney, Agent, or Firm*—Bell, Seltzer, Park & Gibson, P.A.

[57] ABSTRACT

The use of certain herbicidal semicarbazones and salts thereof as potentiators or enhancers of herbicidal and/or plant growth regulating substances.

12 Claims, No Drawings

COMPOSITIONS CONTAINING SEMICARBAZONES

This is a continuation of application Ser. No. 08/400,420, filed Mar. 3, 1995 now U.S. Pat. No. 5,665,673, which is a continuation of application Ser. No. 08/156,503, filed Nov. 23, 1993, now abandoned, which is a continuation-in-part of application Ser. No. 07/972,056, filed Nov. 5, 1992, now abandoned, which is a continuation of application Ser. No. 07/704,684, filed May 17, 1991, now abandoned, which is a continuation of application Ser. No. 07/490,792, filed Mar. 8, 1990, now abandoned, which is a continuation-in-part of application Ser. No. 07/291,850, filed Dec. 29, 1988, now abandoned.

The present invention concerns the use of auxin transport inhibitors as potentiators or enhancers of herbicides, as well as co-application of such auxin transport inhibitors and herbicides, compositions containing at least one auxin transport inhibitor in combination with at least one herbicide and use of these in combatting or controlling undesired plant growth and in plant growth regulation.

Auxin transport inhibitors are compounds which themselves are herbicides and act by inhibiting transmembrane movement of auxin which accumulates in the cells and affects plant growth. Examples of auxin transport inhibitors are e.g. naptalam, TIBA and DPX 1840 (cf E. M. Beyer, Jr. Plant Physiol., 50, 322 (1972), E. M. Beyer, Jr. et al., Plant Physiol., 57, 839 (1976)) and semicarbazones such as described in U.S. Pat. Nos. 5,098,462 and 5,098,466 and EP Patent 219,451. Especially preferred auxin transport inhibitors in the practice of the invention are compounds of formula A:

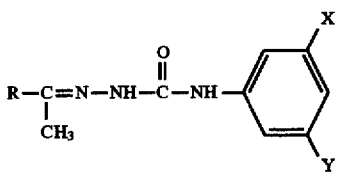

wherein,

X and Y represent independently, hydrogen, fluorine or chlorine, and

R is the group

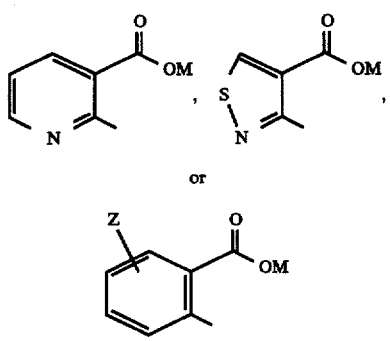

wherein Z is hydrogen, fluorine or chlorine and M is hydrogen, or a salt forming moiety. e.g. an alkali metal cation or an optionally substituted ammonium cation.

Compounds of formula A are generally disclosed, e.g. in U.S. Pat. Nos. 5,098,462 and 5,098,466 and in European Patent No. 219,451, as well as processes for their production, their use as herbicides and plant growth regu-lators and herbicidal and plant growth regulating compositions containing them, the contents of each of which in this respect are incorporated herein by reference. These patents make no reference to the specific compound group of formula A or its potentiating activity.

The term herbicides, as used herein, refers to compounds which combat or control undesired plant growth. This class of compounds may be divided into subclasses according to the primary type or mode of action the herbicide has on the plant. For example according to G. F. Warren of Purdue University, Indiana, USA, herbicides can be classified as auxin transport inhibitors, growth regulator herbicides, photosynthesis inhibitors, pigment inhibitors, growth inhibitors, amino acid synthesis inhibitors, lipid biosynthesis inhibitors, cell wall biosynthesis inhibitors, rapid cell membrane disruptors as well as "miscellaneous" herbicides which do not come under one of the preceding categories. (Growth regulator herbicides include, e.g. auxin agonists.)

In accordance with the present invention it has now surprisingly been found that auxin transport inhibitors, which are usually highly active herbicides in their own right, potentiate the activity of other herbicides on co-application therewith. In the context of this invention herbicides are to be understood as including desiccants and defoliants.

Potentiating, as herein used, refers to the interaction of the auxin transport inhibitor with the herbicide such that the activity is greater than the predicted activity, based upon the activity observed for the auxin transport inhibitor and the herbicide separately. Thus, co-application results in herbicidal activity which is significantly superior to the additive effectiveness of the individual active substances.

This potentiation manifests itself in various forms. Thus, co-application enables application rates to be employed for the auxin transport inhibitor(s) and/or herbicide(s) which would be insufficiently effective if employed alone, or enables various types of weeds to be controlled which would not be controlled by application of each individual active ingredient alone at the same rates as in the mixture.

Furthermore, co-application results in herbicidal activity which is significantly superior to the additive effectiveness of the individual active substances. Moreover, the auxin transport inhibitors of this application are able to increase the efficacy of a herbicide such that the maximum level of control or growth regulation for a given application rate of a herbicide is increased, or alternatively, the application rate of a herbicide giving optimum control or growth regulation can be reduced.

Under co-application is to be understood concurrent, or immediately sequential application (e.g. within 24 hours), application as a tank mix or application of fixed combination premixes.

Non-limiting examples of herbicides which may be potentiated by use of auxin transport inhibitors, especially compounds of formula A in accordance with the invention include 1. other auxin transport inhibitors, e.g. naptalam
2. growth regulators, including 1) benzoic acids, e.g. dicamba; b) phenoxy acids i) acetic acid type, e.g. 2,4-D, MCPA, ii) propionic acid type, e.g. 2,4-DP, MCPP, iii) butyric acid type, e.g. 2,4-DB, MCPB; c) picolinic acids and related compounds, e.g. picloram, triclopyr, fluroxypyr, clopyralid;
3. photosynthesis inhibitors, including a) s-triazines i) chloro substituted, e.g. atrazine, simazine, cyanazine, ii) methoxy substituted, e.g. prometon, iii) methylthio substituted, e.g. ametryn, prometryn; b) other triazines, e.g. hexazinone, metribuzin; c) substituted ureas, e.g. diuron, fluometruon, linuron, tebuthiuron, thidiazuron, forchlorfenuron; d) uracils, e.g. bromacil, terbacil; e) others, e.g. bentazon, desmidepham, methazole, phenmedipham, propanil, pyrazon, pyridate 4. pigment inhibitors, including a) pyridazinones, e.g. norflurazon; b) isoxazolones, e.g. clomazone; c) triketones and cyclic diones of the type described in U.S. Pat. Nos. 4,695,673; 4,921,526; 5,006,150; 5,089,046, U.S. patent application Ser. Nos. 07/411,086 filed on Sep. 22, 1989 and EP 338,992), and 07/994,048 filed on Dec. 14, 1992, now U.S. Pat. No. 5,336,662 and (EP 394,889 and EP 506,907) the contents of each of which are incorporated herein by reference including for example 2-(2-chloro-4-methylsulfonylbenzoyl)-1,3-cyclohexane dione (aka sulcotrione); 2-(4-methylsulfonyloxy-2-nitrobenzoyl)-4,4,6,6-tetramethyl-1,3-cyclohexanedione; 3-(4-methylsulfonyloxy-2-nitrobenzoyl)-bicyclo[3,2,1]octane-2,4-dione; 3-(4-methylsulfonyl-2-nitrobenzoyl)-bicylco [3,2,1]octane-2,4-dione; 4-(4-chloro-2-nitrobenzoyl)-2,6,6-trimethyl-2H-1,2-oxazine-3,5(4H,6H)dione; 4-(4-methylthio-2-nitrobenzoyl)-2,6,6-trimethyl-2H-1,2-oxazine-3,5(4H,6H)-dione; 3-(4-methylthio-2-nitrobenzoyl)-bicyclo[3,2,1]octane-2,4-dione, 4-(2-nitro-4-trifluoromethoxybenzoyl) -2,6,6-trimethyl-2H-1,2-oxazine -3,5(4H,6H) -dione; d) others, e.g. amitrole, fluridone 5. growth inhibitors, including a) milotic disruptors i) dinitroanilines, e.g. trifluralin, prodiamine, benefin, ethalfluralin, isopropalin, oryzalin, pendimethalin; ii) others, e.g. DCPA, dithiopyr, thiazopyr, pronamide; b) inhibitors of shoots of emerging seedlings i) thiocarbamates, e.g. EPTC, butylate, cycloate, molinate, pebulate, thiobencarb, triallate, vernolate; c) inhibitors of roots only of seedlings, e.g. bensulide, napropamide, siduron; d) inhibitors of roots and shoots of seedlings, including chloroacetamides e.g. alachlor, acetochlor, metolachlor, diethatyl, propachlor, and thiophenamines such as dimethenamid (a.k.a. 2-chloro-N-[1-methyl-2-methoxy-ethyl]-N-(2,4-dimethyl-thien-3-yl)acetamide; cf U.S. Pat. No. 4,666,502), and others e.g. cinmethylin 6. amino acid synthesis inhibitors, including a) glyphosate; glufosinate b) sulfonyl-ureas, e.g. metsulfuron, metsulfuron-methyl, ethametsulfuron, nicosulfuron, triasulfuron, primisulfuron, bensulfuron, chlorimuron, chlorimuron-ethyl, chlorsulfuron, sulfometuron, thifensulfuron, tribenuron, triflusulfuron, clopyrasulfuron and pyrazasulfuron; c) sulfonamides, e.g. flumetsulam (a.k.a. DE498); d) imidazolinones, e.g. imazaquin, imazamethabenz, imazapyr, imazethapyr 7. lipid biosynthesis inhibitors, including a) cyclohexanediones, e.g. sethoxydim, clethodium; b) aryloxyphenoxys, e.g. fluazifop-P-butyl, diclofop-methyl, haloxyfop-methyl quizalofop; c) others, e.g. fenoxaprop-ethyl 8. cell wall biosynthesis inhibitors, e.g. dichlobenil, isoxaben 9. rapid cell membrane disruptors, including a) bipyridiliums, e.g. paraquat, diquat; b) diphenyl ethers, e.g. acifluorfen, fomesafen, lactofen, oxyfluorfen; c) glutamine synthetase inhibitors, e.g. glufosinate; d) others, e.g. oxadiazon 10. miscellaneous, including a) carbamates, e.g. asulam; b) nitriles, e.g. bromoxynil, ioxynil; c) hydantocidin and derivatives; d) various, e.g. paclobutrazol, ethofumesate, quinclorac (a.k.a. BAS514), difenzoquat, endothall, fosamine, DSMA, MSMA 11. Others Compounds of the type described in EP 315889 and U.S. patent application Ser. Nos. 07/804,150 filed on Dec. 6, 1991, now abandoned (and EP 461,079 and EP 549,524); and PCT Appln. No. 91/10653 the contents of each of which are incorporated herein by reference including for example 3-[(4,6-dimethoxy-2-pyrimidinyl)hydroxymethyl]-N-methyl-2-pyridine carboxamide; 4,7-dichloro-3-(4,6-dimethoxy-2-pyrimidinyl)-3-hexanoyl-oxyphthalide; 3-[(4,6-dimethoxy-2-pyrimidinyl)carbonyl]-N,N-dimethyl-2-pyridine carboxamide; 3,6-dichloro-2-[(4,6-dimethoxy-2-pyrimidinyl)carbonyl]benzoicacid; 6-chloro-2-[(4,6-dimethoxy-2-pyrimidinyl)thio]benzoic acid (aka DPX-PE350 or pyrithiobac) and salts thereof.

It will be noted that in some cases one auxin transport inhibitor may potentiate the effect of another. The nature of the effect of the auxin transport inhibitor is such that it has the potential to enhance the activity of different classes of herbicides.

The present invention therefore also concerns a method of combatting or controlling undesired plant growth or otherwise regulating plant growth which comprises co-applying to a locus where such combatting or control is desired an herbicidally or plant growth regulating effective aggregate amount of at least one auxin transport inhibitor and at least one other herbicide, wherein the auxin transport inhibitor is applied at a potentiating rate.

Application rates for co-application will of course vary depending upon climatic conditions, season, soil ecology, weeds to be combatted and the like, however, successful results can be obtained e.g. with rates of auxin transport inhibitor of 0.00011 kg to 1.1 kg/ha (0.0001 lb to 1.0 lb/A), preferably 0.0011 to 0.55 kg/ha (0.001 to 0.5 lb/A), especially 0.011 to 0.11 kg/has (0.01 to 0.1 lb/A) in co-application with rates for partner herbicides which correspond to or are significantly lower than recommended for use thereof individually (application rates hereinafter set forth are calculated from measurements originally made in lb/A using the conversion factor 1 lb/A=1.1 kg/ha).

The suitability of specific co-applications for pre- or post-emergent uses and selectivity will of course depend on the partners chosen.

The activity of compounds of formula A is described in the above mentioned patents and that of other known auxin transport inhibitors and of suitable herbicidal partners is described in the literature or on commercially available forms thereof (cf also CROP PROTECTION CHEMICALS REFERENCE, Chemical & Pharmaceutical Press, NY, N.Y.).

The invention also provides herbicidal or plant growth regulating compositions comprising at least one auxin transport inhibitor and at least one other herbicide, wherein the auxin transport inhibitor is present in a potentiating mount. Especially preferred compositions contain a compound of formula A.

Such compositions contain the active substances in association with agriculturally acceptable diluents. They may be employed in either solid or liquid forms e.g. in the form of a wettable powder or an emulsifiable concentrate, incorporating conventional diluents. Such compositions may be produced in conventional manner, e.g. by mixing the active ingredient with a diluent and optionally other formulating ingredients such as surfactants and oils.

The term diluents as used herein means any liquid or solid agriculturally acceptable material which may be added to the active constituent to provide a more easily or improved applicable form, or to achieve a usable or desirable strength of activity. Examples of diluents are talc, kaolin, diatomaceous earth, xylene, non-phytotoxic oils, or water.

Particular formulations, to be applied in spraying forms such as water dispersible concentrates, water dispersible granules, or wettable powders, may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol, a Urea/Ammonium Nitrate mix, a methylated vegetable oil (e.g. SCOIL®—Agsco Inc., Grand Ford, N.D.), an alkylpolyoxyethylene glycol (e.g. X77-Valent, Walnut Creek, Calif.) a buffered crop off (e.g. DASH®, BASF Corp., Parsippanny, N.J.) or an ethoxylated fatty alcohol.

In general, the formulations include from 0.01 to 90% by weight of active agent(s) and from 0 to 20% by weight of agriculturally acceptable surfactant, the active agent consisting either of at least one auxin transport inhibitor and at least one other herbicide. Concentrate forms of compositions generally contain between about 2 and 90%, preferably between about 5 and 80% by weight of active agent. Application forms of formulation may for example contain from 0.01 to 20% by weight of active agent.

When employing concurrent, immediately sequential or tank mix applications the non-auxin transport inhibitor partner(s) can be employed in commercially available form if appropriate and at rates equivalent to or preferably below those recommended by the manufacturer. The auxin transport inhibitor can be formulated as described in the above mentioned EP 219,451, U.S. Pat. Nos. 5,098,462 or 5,098,466.

On co-application according to the present invention other compounds having biological activity, e.g. compounds having insecticidal or fungicidal activity, may also be included.

The preferred modes of application include tank mix prepared e.g. by adding an auxin transport inhibitor to a tank containing the other herbicide partner and an appropriate surfactant and fixed combination premixes.

Depending on the choice of co-application partners both pre- and post-emergent activity on a large range of broadleaf and grassy weeds may be achieved. Non-limiting examples of such weeds are

*Setaria sp.*—foxtail
*Brachiaria platyphylla*—broadleaf signalgrass
*Ipomoea sp.*—morningglories
*Abutilon theophrasti*—velvetleaf
*Hibiscus trionum*—Venice mallow
*Solanum sp.*—nightshades e.g. silverleaf nightshade
*Avena fatua*—wild oats
*Sinapis alba*—white mustard
*Amaranthus sp.*—pigweeds, spiny amaranth
*Xanthium strumarium*—common cocklebur
*Sorghum halepense*—johnsongrass
*Echinochloa crus-galli*—barnyardgrass
*Polygonum sp.*—smartweeds, wild buckwheat, prostrate knotweed
*Cassia obtusifolia*—sicklepod
*Digitaria sp.*—e.g. crabgrasses
*Bromus tectorum*—downy brome
*Apera spica-venti*—windgrass
*Chenopodium album*—common lambsquarter
*Sorghum bicolor*—shattercane
*Portulaca oleracea*—common purslane
*Sida spinos*—prickly sida
*Campsis radicans*—trumpet creeper
*Rottboellia exaltata*—itchgrass
*Cynodon dactylon*—bermudagrass
*Agropyron repens*—quackgrass
*Cyperus sp.*—nutsedges
*Panicum sp.*—prosomillet
*Lespedeza sp*—lespedezas
*Trifolium sp*—clovers
*Hippuris vulgaris*—marestail
*Asclepias sp*—milkweeds
*Salvia sp*—e.g. lanceleaf sage
*Salsola iberica*—russian thistle
*Convolvulus arvensis*—field bindweed
*Cirsium arvense*—Canada thistle
*Proboscidea louisianica*—devils claw
*Senecio sp.*—common Foundsel
*Chorispora tennela*—blue mustard
*Alopecurus myosuroides*—blackgrass
*Sisymbrium altissimum*—tumble mustard
*Caperionia palustris*—texasweed Crop selectivity will also usually depend upon choice of partners. Compounds of formula A for example exhibit excellent selectivity in corn and small grain crops and can also be used in turf and fallow applications.

It will be appreciated that mixtures of an auxin transport inhibitor with more than one other herbicide, e.g. 3-way mixes, are also contemplated.

Preferred auxin transport inhibitors are those of formula A especially those wherein M is hydrogen or a sodium, potassium, isopropylammonium or 2-(2-hydroxy-ethoxy) ethylammonium cation (Compounds $A_1$).

Other compound groups comprise compound of formula A wherein Z represents hydrogen (compounds A2); Z represents fluorine (compounds A3); Z represents chlorine (compounds A4).

Particularly preferred individual auxin transport inhibitors are 2-acetylnicotinic acid 4-(3,5-difluorophenyl) semicarbazone in free acid or in salt form especially its sodium salt form, 2-acetylnicotinic acid 4-(3-fluorophenyl) semicarbazone in free acid form or in salt form especially in sodium salt form, and 2-acetylnicotinic acid-4-(3-chlorophenyl)semicarbazone in free acid form or in sodium salt form.

Preferred classes of herbicidal mix partners are growth regulator herbicides, such as benzoic acids, phenoxy acetic acids, picolinic acids and related compounds, growth inhibitors such as inhibitors of roots and shoots of seedlings, rapid cell membrane disruptors such as bipyridiliums, amino acid synthesis inhibitors such as sulfonylureas and sulfonamides.

Examples of specific, preferred herbicidal partners for co-application are selected from dicamba, thidiazuron, 2,4-D, dimethenamid, atrazine, cyanazine, norflurazon, fluroxypyr, primisulfuron, nicosulfuron, triclopyr, picloram, MCPA, MCPP, pendimethalin, clopyralid, paraquat, ethofumesate, flumetsulam (a.k.a. DE498) and glyphosate.

Non-limiting examples of specific combinations are those containing e.g. 2-acetylnicotinic acid 4-(3,5-difluorophenyl) semicarbazone 2-(2-hydroxyethoxy)ethyl-ammonium salt (a); or 2-acetylnicotinic acid, 4-(3-fluorophenyl) semicarbazone sodium salt (b); or 2-acetylnicotinic acid 4-(3-chlorophenyl)semicarbazone sodium salt (c); 2-acetylnicotinic acid 4-(3,5-difluorophenyl)semicarbazone (d); 2-acetylnicotinic acid 4-(3,5-difluorophenyl) semicarbazone sodium salt (e); each with e.g. dicamba (z); dimethenamid (y); 2,4-D (x); or thidiazuron (w).

As stated above, application rates may depend on a variety of factors. In general, satisfactory, results are obtained when applying the co-application partners at the rates given below:

Compound (a), (b), (c) or (d) 0.0011 to 1.1 kg/ha preferably 0.011 to 0.55 kg/ha, especially 0.011 to 0.11 kg/ha.

Compound (z) 0.011 to 2.2 kg/ha, preferably 0.05 to 0.55 kg/ha, especially 0.11 to 0.55 kg/ha.

Compound (y) 0.11 to 4.4 kg/ha, preferably 0.275 to 1.0 kg/ha, especially 0.55 to 1.0 kg/ha.

Compound (x) 0.011 to 2.2 kg/ha, preferably 0.11 to 1.1 kg/ha, especially 0.275 to 0.825 kg/ha.

Compound (w) 0311 to 1.1 kg/ha, preferably 0.055 to 0.55 kg/ha, especially 0.088 to 0.44 kg/ha.

The weight ratio of individual components in fixed premixes will vary according to the intended application rate thus for example, the ratio of compound (a) to compound (z) in a premix may vary e.g. from 1:2000 to 100:1, preferably 1:50 to 5:1, especially 1:50 to 1:1 e.g. 1:50 to 1:2.5.

Examples of a 3-way mixtures are compound (e) with compound (z) and nicosulfuron, dimethenamid or glyphosate.

Also for example a mixture of compound (d) or a salt thereof with compound (z) may have added thereto a grass active herbicide such as from classes 5 and 7 listed above.

The compounds of formula A wherein Z is chlorine or fluorine are new and also form part of the invention. The invention therefore further concerns compounds of formula XA

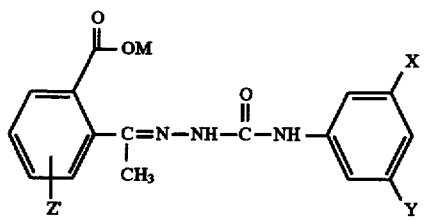

wherein X, Y and M are as defined for formula A and Z' represents chlorine or fluorine.

The invention also concerns use of compounds of formula XA alone or in combination with other active compounds in combatting weeds, herbicidal compositions containing compounds of formula XA either alone or in combination with other active compounds and processes for preparing compounds of formula XA.

Particular compounds of formula XA are for example those wherein X is fluorine or chlorine, Y is hydrogen or fluorine and Z is 6-fluorine or 6-chlorine (ortho to carboxylic) in salt or free acid form.

Compounds of formula XA wherein Z' is 6-fluorine or 6-chlorine are particularly preferred.

The use of compounds of formula XA and their formulation as herbicidal compositions can be carried out as described herein or as described in U.S. Pat. Nos. 5,098,462; 5,098,466 and in European Patent No. 219,451, the contents of each of which in this respect are incorporated herein by reference.

The following examples are intended to illustrate without in any way limiting the invention.

EXAMPLE 1

Field Test

A field trial was conducted against velvetleaf and pigweed in field corn. Application was post-emergent 35 days after seeding with weeds at a height of 41 to 89 cm. Application was of tank mixed formulation by foliar applied broadcast treatment. Compound (a) above was tank mixed as is. Compound (z) above was tank mixed in the form of a 0.5 kg/l s.c. commercially available under the trademark BANVEL®. Aquagene is a commercially available surfactant, (Universal Coop Incorporated, Minneapolis, Minn.). Values set forth are calculated from measurements originally made in acres, lbs, inches and gallons according to the conversion factors: 1 hectare=2.47 acres; 1 kg=2.2 lbs; m=3.28 ft; and 1 gallon=3.78 l.

The results may be summarized as follows.

| Treatment | Rate kg/ha | % of control Velvetleaf | Pigweed |
|---|---|---|---|
| Aquagene[1] | 0 | 0 | 0 |
| Compound (z) | 0.275 | 18 | 30 |
| Compound (a) | 0.011 | 13 | 18 |
| Compound (z) + Aquagene[1] | 0.275 | 27 | 40 |
| Compound (a) + Aquagene[1] | 0.011 | 13 | 18 |
| Compound (a) + Compound (z) | 0.011 0.275 | 57 | 90 |
| Compound (a) + Compound (z) Aquagene[1] | 0.011 0.275 | 65 | 93 |

[1] 0.9 l/ha

The tank mix combination of (a) plus (z) was significantly better than either treatment alone. The adjuvant provided some increase in control, but was not responsible for the surprising increase in control observed for the herbicide combination. The combination of (a) plus (z) yielded a response markedly superior to the additive effect of either herbicide which when applied alone at the stated rate showed unsatisfactory weed control.

There was no significant effect on the field corn.

EXAMPLE 2

Greenhouse Test

A greenhouse test was conducted against velvetleaf, pigweed, morningglory and cocklebur. Treatment was at 10 days post-emergence and evaluation at 18 days after treatment. Compound (e) was formulated as technical a.i. in a mixture of equal parts acetone and water with ½% surfactant. Compound (z) was used in the commercially available form BANVEL® herbicide (=480 g/L a.i. equivalent) in water with ½% surfactant. The tank mixes were applied in a linear spray chamber with 3 repetitions per concentration.

| Treatment | Rate kg/ha | % control Velvetleaf | Pigweed | Morningglory | Cocklebur |
|---|---|---|---|---|---|
| Compound (e) | 0.01 | 55 | 50 | 55 | 25 |
| Compound (z)* | 0.02 | 35 | 35 | 35 | 75 |
| Compound (e) + Compound (z) | 0.01 0.02 | 98 | 100 | 98 | 100 |

*as the commercially available BANVEL ® herbicide.

The results indicate synergism utilizing Limpel's formula and are statistically significant utilizing Duncan's multiple range test.

EXAMPLE 3

Preparation of 2-aceyl-6-fluorobenzoic acid 4-(3,5-difluorophenyl)semicarbazone (Table A cpd 1)

a) Preparation of 3-fluorophthalic anhydride 15 g of 3-fluorophthalic acid are mixed with 16.6 g of acetic anhydride and refluxed for 3 hrs. After removal of unreacted acetic anhydride the remaining white solid is recrystallized from toluene.

b) Preparation of 2-acetyl-6-fluorobenzoic add 9 g of 3-fluorophthalic anhydride and 6.8 g of malonic acid are mixed in 80 ml of triethylamine and heated in an oil bath at 71°–72° until evolution of gas ceases. The reaction mixture is mixed with 50 ml of 10% HCl/H$_2$O and extracted with ether. The ether is evaporated off and the resulting black oil chromatographed on a column using 1 l of 20% of ethylacetate/hexane followed by 1 l of 30% ethylacetate/hexane to yield first the 3-fluoro-isomer followed by the desired 6-fluoro isomer; m.p. 76°81.5°.

c) Preparation of title compound 3 g of 6-fluoro-2-acetyl benzoic acid and 3 g of 4-(3,5-difluorophenyl)-semicarbazide are mixed in 20 ml of methanol and heated until clear. The solution is then stirred at R.T. for 24 hr. A white solid forms which is filtered and dried in vacuum at 60° to yield the title product m.p. 227° (decomp.). The corresponding sodium salt is made by reaction of the free acid with 25% sodium methoxylate/methanol.

The following compounds of formula XA may be prepared analogously.

TABLE A

| Cpd no | X | Y | Z' | m.p. |
|---|---|---|---|---|
| 1 | F | F | 6-F | acid 227° (decomp) Na$^+$ salt |
| 2 | F | H | 6-F | acid 174° (decomp) |
| 3 | Cl | H | 6-F | acid 157° (decomp) |
| 4 | F | F | 6-Cl | acid 174° (decomp) |
| 5 | F | H | 6-Cl | acid 176° (decomp) |
| 6 | Cl | H | 6-Cl | acid 204° (decomp) |

What is claimed is:

1. A herbicidal composition comprising a herbicidally effective aggregate amount of an auxin transport inhibitor of the formula A

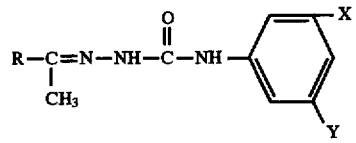

wherein,

X and Y represent independently hydrogen, fluorine or chlorine and R is the group

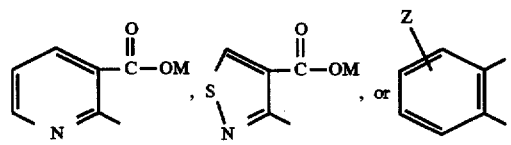

wherein Z is hydrogen, fluorine or chlorine and M is hydrogen or a salt forming moiety and one other herbicide wherein the herbicide is a phenoxy acetic acid and the auxin transport inhibitor is present in an amount producing a potentiating effect.

2. A herbicidal composition according to claim 1 wherein the herbicide is 2,4D or MCPA.

3. A herbicidal composition according to claim 1 wherein in the auxin transport inhibitor of formula A, M is hydrogen or a sodium, potassium, isopropylammonium or 2-(2-hydroxyethoxy)ethylammonium cation.

4. A herbicidal composition according to claim 1 wherein the auxin transport inhibitor is 2-acetylnicotinic acid 4-(3,5-difluorophenyl)semicarbazone, 2-acetylnicotinic acid 4-(3-fluorophenyl)semicarbazone or 2-acetylnicotinic acid 4-(3-chlorophenyl)semicarbazone in free acid or in salt form.

5. A herbicidal composition according to claim 1 wherein the auxin transport inhibitor is 2-acetylnicotinic acid 4-(3,5-difluorophenyl)semicarbazone 2-(2-hydroxyethoxy)ethylammonium salt (a); or 2-acetylnicotinic acid 4-(3-fluorophenyl)-semicarbazone sodium salt (b); 2,acetylnicotinic acid 4-(3-chlorophenyl)semicarbazone sodium salt (c); or 2-acetylnicotinic acid 4-(3,5-difluorophenyl)semicarbazone (d) and the herbicide is 2,4-D.

6. A herbicidal composition according to claim 1 wherein the herbicide is 2,4-D and the R group of formula A is the pyridyl group.

7. A herbicidal composition according to claim 1 wherein the R group of formula A is the pyridyl group.

8. A herbicidal composition according to claim 1 wherein the weight ratio of auxin transport inhibitor to the other herbicide is 1:50 to 1:1.

9. A herbicidal composition according to claim 8 wherein the weight ratio of auxin transport inhibitor to the other herbicide is 1:50 to 1:2.5.

10. A method for combating or controlling undesired plant growth comprising co-applying to a locus where said combating or control is desired the herbicidal composition according to claim 1.

11. A method according to claim 10 wherein the auxin transport inhibitor is applied at a rate of 0.0011 to 1.1 kg/ha.

12. A method of potentiating the herbicidal effect of 2,4-D comprising combining 2,4-D with a potentiating effective amount of an auxin transport inhibitor of formula A

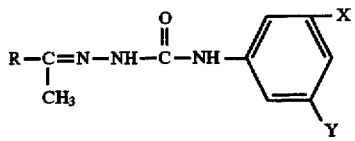

wherein X and Y represent independently, hydrogen, fluorine or chlorine and R is the group

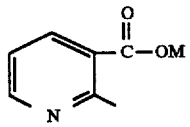

wherein M is hydrogen or a salt forming moiety and weight ratio of the auxin transport inhibitor to 2,4-D is from 1:50 to 5:1, to produce a herbicidally effective composition.

* * * * *